United States Patent [19]

Scheller et al.

[11] Patent Number: 5,089,256

[45] Date of Patent: Feb. 18, 1992

[54] PROCESS FOR PREPARING SOLID POWDER FORMULATIONS HAVING DIFFERENT COLORS

[75] Inventors: Hans U. Scheller; Karl A. Scheller, both of Eislingen/Fils, Fed. Rep. of Germany

[73] Assignee: Württembergische Parfümerie-Fabrik GmbH, Eislingen, Fed. Rep. of Germany

[21] Appl. No.: 296,027

[22] Filed: Jan. 12, 1989

Related U.S. Application Data

[63] Continuation-in-part of Ser. No. 388,558, Nov. 18, 1988, abandoned.

[30] Foreign Application Priority Data

Aug. 5, 1986 [EP] European Pat. Off. ......... 86/110823

[51] Int. Cl.⁵ .................... A61K 7/03; B65D 81/32
[52] U.S. Cl. .......................... 424/63; 424/64; 424/69; 264/245; 264/250; 425/131.1
[58] Field of Search ............... 424/63, 69, 61, 64; 264/250, 245; 425/131.1, DIG. 32

[56] References Cited

U.S. PATENT DOCUMENTS

| 4,650,672 | 3/1987 | Yagita et al. | 424/63 |
| 4,752,496 | 6/1988 | Fellows et al. | 424/63 X |
| 4,786,449 | 11/1988 | Smit | 264/245 |
| 4,804,538 | 2/1989 | Chen | 424/63 |
| 4,887,409 | 12/1989 | Israel et al. | 264/245 X |

FOREIGN PATENT DOCUMENTS

| 0135060 | 3/1985 | European Pat. Off. | |
| 2349051 | 4/1975 | Fed. Rep. of Germany | |
| 6067405 | 9/1983 | Japan | 424/63 |
| 1486634 | 9/1977 | United Kingdom | 424/63 |

Primary Examiner—Thurman K. Page
Assistant Examiner—Donald R. McPhail
Attorney, Agent, or Firm—Wegner, Cantor, Mueller & Player

[57] ABSTRACT

The process for the preparation of containers comprising two or more partial regions separated from each other of solid cast powder formulations having different colors employs containers into which separating bridges of a pasty composition have been injected, said composition being similar to the subsequently cast solid powder formulations. The bridges prevent the partial regions having different colors from coalescing.

20 Claims, No Drawings

PROCESS FOR PREPARING SOLID POWDER FORMULATIONS HAVING DIFFERENT COLORS

This application is a continuation-in-part of U.S. Ser. No. 388,558 filed Nov. 18, 1988, now abandoned.

The present invention relates to a process for the preparation of containers comprising two or more regions, separated from each other, of solid cast powder formulations having different colors. More specifically, it relates to regions, separated from each other, of solid cast powder formulations having different colors according to the European Patent Application No. 84 108 763.8 (Publication No. 0 135 060) or U.S. Pat. Application Ser. No. 130,523, filed Dec. 9, 1987, which contain
a) one or several filler(s),
b) one or several fatty and waxy component(s),
c) one or several active ingredient(s) and or colorant(s),
d) one or several evaporable non-toxic hydrophobic solvents and,
e) optionally, further additives.
which is characterized in that the filler(s) comprise(s) (a) non-hydroscopic flowable organic or inorganic solid(s) having a particle size of from 5 to 50 $\mu$m in diameter.

Containers with two or more regions separated from each other of solid cast powder formulations having different colors could so far be manufactured only if several containers mutually fitting with each other were present or if separating bridges had been inserted in advance or injected into said containers. This at least requires an accordingly high expense for injecting tools or the mounting of several receiving molds (pans) in the containers.

It is the object of the invention to develop a process by which two or more regions separated from each other of solid cast powder formulations having different colors can be cast into containers without allowing the colors to coalesce and be mixed. It is another object to avoid a qualitative change to occur in the solid cast powder preparations. Furthermore, the process should be as simple as possible but nevertheless flexibly applicable so as to permit the realization not only of straight, but also of bent and wavy separating lines between the differently colored partial regions of the powder preparations.

The objects defined above could be attained in a surprisingly easy way by developing injectable pasty mixes having compositions similar to those of finished cast powder preparations and then injecting said mixes as separating bridge areas into the containers. After the pass bridges have been injected, powder formulations having different colors may be cast into the various regions or compartments formed within the containers by the separating bridge areas, whereupon the excess of the solvent is evaporated and, if desired, the surfaces of the products thus obtained are treated with pressures of less than 10 bar.

Thus, the present invention provides a process for the preparation of containers with two or more separated partial regions or compartments of solid cast powder formulations having different colors, which process is characterized in that I. separating bridges of a pasty composition are injected into the containers, said composition containing
   a) from 0 to 20 by weight of a non-hydroscopic flowable organ solid having a particle size of from 5 to 50 $\mu$m as filler,
   b) one or more fat-like or waxy components,
   c) a colored or color-neutral pigment or pearlescent pigment,
   d) one or more evaporable non-toxic hydrophobic solvent(s),
   e) optionally further conventional additives for castable solid powder preparations,
whereafter
II. powder formulations having different colors are poured into the various regions or compartments formed within the containers by the separating bridge areas,
whereafter
III. the excess of the solvent is evaporated and, if desired, the surfaces of the products thus obtained are treated with pressures of less than 10 bar.

Since the composition is intended to correspond to the composition of the meanwhile commercially available solid cast powder preparations according to European Patent Application No. 84 108 763.8 (EP-AI 0 135 060), U.S. Pat. Application Ser. No. 130,523, filed Dec. 9, 1987, the filler preferred to be used is Nylon-12 powder substantially containing spherical or ellipsoidal bodies. The bulk density mostly is from 0.20 to 0.35. The density mostly is from 1.00 to 1.03. Said Nylon 12 powder is employed in an amount of between 7.0 and 20% by weight, and preferably of about 8% by weight. More specifically, if polysiloxane/polyalkyl polyether copolymers are employed as a further component in an amount of from 10 to 20% by weight, the fillers according to feature a) may be completely omitted.

As the fat-like and waxy components there are preferably used oleyl erucate, stearic acid monoethanolamide and glyceryl oleate. The preferred amounts are from 3.0 to 5% by weight, and particularly about 4% by weight, of oleyl erucate, from 0.8 to 2.0% by weight, and particularly about 1% by weight, of stearic acid monoethanolamide, and from 0.4 to 2.0% by weight, and particularly about 0.5% by weight, of glyceryl stearate and/or oleate. Further usable are mixtures of bees' wax, stearic acid monoethanolamide and microcrystalline hard wax. They are mostly used in an amount of from 6 to 8% by weight of each.

The amount of colored or color-neutral pigment or pearlescent pigment preferably is between 40 and 50% by weight, and particularly about 43% by weight. More specifically, if no fillers according to feature a) are employed, the amount of colored or color-neutral pigment or pearlescent pigment may also be reduced to from 8 to 15% by weight.

As the evaporable non-toxic hydrophobic solvent there is preferably used octamethyl cyclotetrasiloxane, namely in an amount of from 35.0 to 45.0% by weight. If no fillers according to feature a) are present, the solvent content may be increased to from 50 to 60%.

As further conventional additives for castable solid powder preparations there are employed, also in accordance with the present invention, about 0.1% by weight of methyl paraben, about 0.1% by weight of propyl paraben, about 0.1% by weight of methylchloroisothiazolinone and methylisothiazolinone, and about 0.05% of butylhydroxytoluene. If it is intended to omit fillers according to the feature a), then 10 to 20% by weight of polysiloxane/polyalkyl polyether copolymers are employed in combination with organic non-ionic emulsifiers.

Thus, in comparison to the conventional recipes for the solid powder compositions to be cast, the recipes for the injectable pasty compositions comprise lesser amounts of fat-like and waxy components and of Nylon powder, but higher amounts of pigment and/or pearlescent pigment and/or, as a further additive according to feature e), polysiloxane,polyalkyl polyether copolymers in combination with organic non-ionic emulsifiers. Thereby, non-fluid but strand-forming pasty products are obtained, of which bridges may be injected into the containers by means of an injection nozzle. These bridges may be straight, but also bent or curved. These pasty bridges will not even re-melt at subsequent working temperatures of up to 80° C. However, they are capable of bonding to the liquid cast powder preparations to form a uniform solid powder after the drying procedure. They mostly form a separating layer which is optically hardly or not at all visible and exhibits an absolutely indifferent behavior upon subsequent use. If they do not contain colorant pigments, but only color-neutral pigments or pearlescent pigments, any mixing of colors will not be observed. However, even if they show a color of their own due to colored pigments, no disorderly mixing is observed.

Thus, by use of the process according to the invention it is possible in a larger container to prepare two or more regions separated from each other and different in color and thereby to create appealing shapes and ornaments. The process is easier and more economical than manufacturing containers with separating bridges, all the more so because individual injection tools or deep-draw molds would have to be provided for each designed shape.

The following Examples present preferred recipes for the injectable pasty composition, said recipes being particularly well suitable for the commercial products which are already being marketed. However, it is basically possible according to the European Patent Application No. 84 108 763.8 (EP-AI 0 135 060) U.S. Pat. Application Ser. No. 130,523, filed Dec. 9, 1987 to prepare various cast powder preparations, so that other injectable pasty compositions can be designed and used.

EXAMPLE 1

An injectable pasty composition for casting bridges in containers has the composition as follows:

| | |
|---|---|
| Oleyl erucate | 4.0% |
| Stearic acid monoethanolamide | 1.0% |
| Glyceryl stearate/or oleate | 0.5% |
| Nylon-12 powder | 8.0% |
| Color-neutral pigment/ pearlescent pigment | 43.15% |
| Octamethyl cyclotetrasiloxane | 43.0% |
| Methylhydroxytoluene | 0.05% |
| Methyl chloroisothiazolinone + methylisothiazolinone | 0.10% |
| Methyl paraben | 0.10% |
| Propyl paraben | 0.10% |
| | 100.00% |

The above mixture may be extruded at room temperature or a temperature of up to 40° C. from a die as a strand into a container, the diameter of the extruded strand corresponding to about the layer thickness of the subsequent powder. Immediately thereafter, the powder compositions having various colors may be cast into the compartments formed thereby in a per se known manner. The containers are layer-wise placed in a drying oven and allowed to sit there for about 5 to 10 hours, whereby the major portion of the octamethyleyclotetrasiloxane is evaporated. If desired, the surface of the products thus obtained is treated with a pressure of below 10 bar.

EXAMPLE 2

Another injectable pasty composition for casting bridges in containers has the composition as follows:

| | |
|---|---|
| Bees' wax | 7.0% |
| Stearic acid monoethanolamide | 7.0% |
| Microcrystalline hard wax (Lunacera ® 80) | 7.0% |
| Cetyl dimethicone copolyol, cetyl dimethicone, polyglyceryl-3-oleate, hexyl laurate (Abil ® WS 08) | 15.0% |
| Octamethyl cyclotetrasiloxane | 54.0% |
| Color-neutral pigment/ pearlescent pigment | 10.0% |
| | 100.00% |

The components are first mixed in the absence of the solvent and pigment and melted. Then the solvent and pigment are added, and the composition is blended until it is homogeneous. As is described in Example 1, the mixture is extruded at room temperature or a temperature of up to 40° C. from a die as a strand into a container and further processed. This composition, more specifically, can be trouble-free processed at elevated pressures, whereby no segregation does occur. The behavior in the drying procedure corresponds to that of the powder composition.

EXAMPLE 3

Other injectable colored pasty compositions for casting bridges in containers have the compositions as follows:

| | Range | Preferred amount |
|---|---|---|
| Cetyl dimethicone copolyol, cetyl dimethicone, polyglyceryl-3-oleate, hexyl laurate | 13–20% | 17% |
| Stearic acid monoethanolamide | 1–5% | 2% |
| Glyceryl stearate/or oleate | 2–6% | 4% |
| Colorant pigment | 3–10% | 9% |
| Nylon-12 powder | 5–10% | 8% |
| Octamethyl cyclotetrasiloxane | 40–50% | 32% |
| Color-neutral or colored pearlescent pigment | 20–40% | 28% |
| | | 100% |

The above formulation is process in the same manner as in Example 2.

The following powder formulations are disclosed in U.S. Ser. No. 130,523, filed Dec. 9, 1987.

EXAMPLE 1

A fluid composition for preparing a solid powder preparation has the composition as follows:

| | |
|---|---|
| Oleyl erucate | 7.20% by weight |
| Stearic acid monoethanolamide | 1.00% by weight |
| Glyceryl oleate | 2.00% by weight |
| Methyl paraben | 0.20% by weight |
| Propyl paraben | 0.10% by weight |
| Butylhydroxytoluene (antioxidant) | 0.10% by weight |
| Nylon-12 powder | 12.00% by weight |
| Cyclomethicone* | 48.70% by weight |
| Methylchloroisithiazolinone + | 0.20% by weight |

| | |
|---|---|
| -continued | |
| methylisothiazolinone | |
| Pigments and pearl pigments | 28.50% by weight |
| | 100.00% by weight |

*octamethylcyclotetrasiloxane

The Nylon-12 powder consists of mostly spherical and ellipsoidal particles having a bulk density of from 0.20 to 0.35 g/cm$^3$ and a density of from 1.02 to 1.03 g/cm$^3$. The particle size distribution is as follows:

| Proportion of particles | |
|---|---|
| larger than 40 μm | less than 0.5% |
| 40 to 30 μm | less than 6.0% |
| 30 to 20 μm | less than 10.0% |
| 20 to 10 μm | more than 40.0% |
| 10 to 5 μm | more than 30.0%. |

In consideration of the standard deviation of 3.51 μm there results an average particle size of the powder of 12.1 μm. The powder is hydrophobic and takes up a maximum 1% moisture from air.

Part of the wax and fat is used for stirring the pigments such as to give a homogeneous dye paste. The remaining portion is charged into a double-walled vessel equipped with a stirred and dispergator. The antioxidant and the preservatives are further charged into the vessel, and the contents is heated and melted at 85° C. Then the dye pastes comprising the pigments and part of the wax and fat phases are added with stirring to give a homogeneous product. The temperature is maintained at 80° C. to 85° C. Now the silicone oil having been left at room temperature together with the preservative methylchloroisithiazolinone+methylisothiazolinone which is sensitive towards elevated temperature are added and the mixture is stirred until it is homogeneous. Then the Nylon powder is added as a powder with stirring, followed by the addition of the dry pearl pigment. In the homogenization procedure the temperature will be allowed to drop to 75° C. With proper handling it is not necessary to deaerate the casting composition. In the case that air inclusions due to incautions operation are detactable, these may be removed by applying a slightly reduced pressure of a minimum of 0.5 bar. Now, the casting composition is complete and is allowed to flow into a casting machine comprising an automatically operating portioning custom to fill powder boxes at a temperature of 75° C. Depending on size and dimensions of the boxes it may be required to preheat same at about 30° C. by means of dry hot air so that in the course of inflow of the casting composition the temperature will not drop to below 45° C. After about 1 to 2 minutes and cooling to a tmeperature between 45° C. the cast mass will solidify to give a semi-solid cream. The filled molds are then put in layers into a drying cabinet at 60° C. through which a strong stream of air is circulated and kept therein for about 15 hours. The permanently flowing air stream entrains the slowly evaporating volatile silicone oil. It is removed form the circulating air by means of subsequently located washing columns kept cool and filled with the same silicone oil and may be re-used.

The drying step is completed as soon as the powder composition has been completely solidified, while, however, the powder on the surface is still removable and spreadable as softly as silk and very thinly by means of an applicator or the dry finger tip. The content of silicone oil amounts to a maximum of 5%, preferably to from 2 to 3%.

The surface of the cast molds may be marked by means of a stamp with a pressure of about 5 bar or be decorated with a texture pattern.

When 0.20 to 0.50% by weight of a perfume are to be added, the amount of silicone oil is correspondingly reduced.

EXAMPLES 2 AND 3

In a manner analogous to that described in Example 1', the components listed hereafter were processed together to give solid powder preparations.

| | Example 2' % by weight | Example 3' % by weight |
|---|---|---|
| Oleyl erucate | 7.20 | 7.20 |
| Stearic acid monoethanolamide | 1.00 | 1.00 |
| Glyceryl oleate | 2.00 | 2.00 |
| Methyl paraben | 0.20 | 0.20 |
| Propyl paraben | 0.10 | 0.10 |
| Butylhydroxytoluene (antioxidant) | 0.10 | 0.10 |
| Tricalcium phosphate | 12.00 | — |
| Polyethylene | — | 15.00 |
| Cyclomethicone | 56.20 | 53.20 |
| Methylchloroisthiazolinone + methylisothiazolinone | 0.20 | 0.20 |
| Pigments and pearl pigments | 21.00 | 21.00 |
| | 100.00 | 100.00 |

The average particle diameter of the tricalcium phosphate was 6 to 8 μm. The average diameter of the polyethylene powder was 6 μm. When perfume was added, the portion of silicone oil was correspondingly reduced.

We claim:

1. A process for preparing a container which comprises separate compartments containing powder formulations of different colors, said process comprising:
   (I) injecting a separating bridge into the container such that said separating bridge forms a first and a second compartment in the container wherein each of said first and second compartments are separated by said separating bridge, said separating bridge comprising a paste composition which comprises:
      (a) from 0 to *% by weight of a nonhygroscopic flowable organic solid having a particle size of from 5 to 50 μm as a filler;
      (b) a fatty acid, a derivative thereof or a wax;
      (c) a colored or color-neutral pigment or pearlescent pigment; and
      (d) an evaporable non-toxic hydrophobic solvent;
   (II) pouring a first powder formulation in said first compartment and a second powder formulation in said second compartment, said first powder formulation having a different color than said second powder formulation; and
   (III) evaporating the excess of said solvent.

2. The process according to claim 1, further comprising treating surfaces of the product obtained from step (III) with a pressure of less than 10 bar.

3. The process according to claim 1, wherein said nonhydroscopic flowable organic solid comprises spherical or ellipsoidal particles of polyamide 12 powder present in said composition at 7 to 20% by weight.

4. The process according to claim 1, wherein said fatty acid, derivative thereof or wax is selected from the group consisting of oleyl eructate, stearic acid monoethanolamide, glyceryl oleate, bees wax, microcrystalline hard wax, and mixtures thereof.

5. The process according to claim 1, wherein said solvent comprises octamethyl cyclotetrasiloxane.

6. The process according to claim 1, wherein said paste composition further comprises at least one member selected from the group consisting of methylparaben, propylparaben, butylhydroxytoluene, methylchloroisothiazolinone/methylisothiazolinone copolymers and polysiloxane/polyalkyl polyether copolymers, in combination with an organic non-ionic emulsifier.

7. The process according to claim 6, wherein said emulsifier is selected from the group consisting of cetyl dimethicone copolyol, cetyl dimethicone, polyglyceryl-3-oleate and hexyl laurate.

8. The process according to claim 4, wherein said paste composition further comprises at least one member selected from the group consisting of methylparaben, propylparaben, butylhydroxytoluene, methylchloroisothiazolinone/methylisothiazolinone copolymers and polysiloxane/polyalkyl polyether copolymers, in combination with an organic non-ionic emulsifier.

9. The process according to claim 3, characterized in that the paste composition employed is a mixture comprising
   a) 7.0 to 15% by weight of polyamide 12 powder;
   b) 3.0 to 5.0% by weight of oleyl erucate; 0.8 to 2.0% by weight of stearic acid monoethanolamide;
   c) 40 to 50% by weight of color-neutral pigment and/or oleate
   d) 35 to 45% by weight of octamethyl cyclotetrasiloxane;
   e) about 0.1% by weight of methylparaben; about 0.1% by weight of propylparaben; about 0.1% by weight of methylchloroisothiazolinone and methylisothiazolinone; about 0.05% by weight of butylhydroxytoluene.

10. The process according to claim 4, characterized in that the paste composition employed is a mixture comprising
   a) 7.0 to 15.0% by weight of polyamide 12 powder;
   b) 3.0 to 5.0% by weight of oleyl erucate; 0.8 to 2.0% by weight of stearic acid monoethanolamide;
   c) 40 to 50% by weight of color-neutral pigment and/or oleate
   d) 35 to 45% by weight of octamethyl cyclotetrasiloxane;
   e) about 0.1% by weight of methylparaben; about 0.1% by weight of propylparaben; about 0.1% by weight of methylchloroisothiazolinone and methylisothiazolinone; about 0.05% by weight of butylhydroxytoluene.

11. The process according to claim 5, characterized in that the paste composition employed is a mixture comprising
   7.0 to 15.0% by weight of polyamide 12 powder;
   b) 3.0 to 5.0% by weight of oleyl erucate; 0.8 to 2.0% by weight of stearic acid monoethanolamide;
   c) 40 to 50% by weight of color-neutral pigment and/or oleate
   d) 35 to 45% by weight of octamethyl cyclotetrasiloxane;
   e) about 0.1% by weight of methylparaben; about 0.1% by weight of propylparaben; about 0.1% by weight of methylchloroisothiazolinone and methylisothiazolinone; about 0.05% by weight of butylhydroxytoluene.

12. The process according to claim 6, characterized in that the paste composition employed is a mixture comprising
   a) 7.0 to 15.0% by weight of polyamide 12 powder;
   b) 3.0 to 5.0% by weight of oleyl erucate; 0.8 to 2.0% by weight of stearic acid monoethanolamide;
   c) 40% to 50% by weight of color-neutral pigment and/or oleate
   d) 35 to 45% by weight of octamethyl cyclotetrasiloxane;
   e) about 0.1% by weight of methylparaben; about 0.1% by weight of propylparaben; about 0.1% by weight of methylchloroisothiazolinone and methylisothiazolinone; about 0.05% by weight of butylhydroxytoluene.

13. The process according to claim 1, characterized in that the paste composition employed is a mixture comprising
   b) 8 to 8% by weight of bees' wax; 6 to 8% by weight of stearic acid monoethanolamide;
   c) 8 to 15% by weight of color-neutral pigment and/or pearlescent pigment;
   d) 50 to 60% by weight of octamethyl cyclotetrasiloxane;
   e) 10 to 20% by weight of polysiloxane/polyalkyl polyether copolymers in combination with organic non-ionic emulsifiers.

14. The process according to claim 4, characterized in that the paste composition employed is a mixture comprising
   b) 6 to 8% by weight of bees' wax; 6 to 8% by weight of stearic acid monoethanolamide;
   c) 8 to 15% by weight of color-neutral pigment and/or pearlescent pigment;
   d) 50 to 60% by weight of octamethyl cyclotetrasiloxane;
   e) 10 to 20% by weight of polysiloxane/polyalkyl polyether copolymers in combination with organic non-ionic emulsifiers.

15. The process according to claim 5, characterized in that the paste composition employed is a mixture comprising
   b) 6 to 8% by weight of bees' wax; 6 to 8% by weight of stearic acid monoethanolamide;
   c) 8 to 15% by weight of color-neutral pigment and/or pearlescent pigment;
   d) 50 to 60% by weight of octamethyl cyclotetrasiloxane;
   e) 10 to 20% by weight of polysiloxane/polyalkyl polyether copolymers in combination with organic non-ionic emulsifiers.

16. The process according to claim 6, characterized in that the paste composition employed is a mixture comprising
   b) 6 to 8% by weight of bees' wax;
   6 to 8% by weight of stearic acid monoethanolamide;
   c) 8 to 15% by weight of color-neutral pigment and/or pearlescent pigment;
   d) 50 to 60% by weight of octamethyl cyclotetrasiloxane;
   e) 10 to 20% by weight of polysiloxane/polyalkyl polyether copolymers in combination with organic non-ionic emulsifiers.

17. The process according to claim 3, characterized in that the pasty, composition employed is a mixture comprising a) 13 to 20% by weight of polyamide 12 powder;
b) 1 to 5% by weight of stearic acid monoethanolamide;
2 to 6% by weight of glyceryl stearate / or oleate;
c) 3 to 10% by weight of colorant pigment;
20 to 40% by weight of color-neutral or colored pearlescent pigment;
d) 40 to 50% by weight of octamethyl cyclotetrasiloxane;
13 to 20% by weight of cetyl dimethicone copolyol, cetyl dimethicone, polyglyceryl-3-oleate, hexyl laurate.

18. The process according to claim 4, characterized in that the paste composition employed is a mixture comprising
a) 13 to 20% by weight of polyamide 12 powder;
b) 1 to 5% by weight of stearic acid monoethanolamide;
2 to 6% by weight of glyceryl stearate / or oleate;
c) 3 to 10% by weight of colorant pigment;
20 to 40% by weight of color-neutral or colored pearlescent pigment;
d) 40 to 50% by weight of octamethyl cyclotetrasiloxane;
e) 13 to 20% by weight of cetyl Dimethicone copolyol, cetyl dimethicone, polyglyceryl-3-oleate, hexyl laurate.

19. The process according to claim 5, characterized in that the paste composition employed is a mixture comprising
a) 13 to 20% by weight of polyamide powder;
b) 1 to 5% by weight of stearic acid monoethanolamide;
2 to 6% by weight of glyceryl stearate / or oleate;
c) 3 to 10% by weight of colorant pigment;
20 to 40% by weight of color-neutral or colored pearlescent pigment;
d) 40 to 50% by weight of octamethyl cyclotetrasiloxane;
e) 13 to 20% by weight of cetyl dimethicone copolyol, cetyl dimethicone, polyglyceryl-3-oleate, hexyl laurate.

20. The process according to claim 6, characterized in that the paste composition employed is a mixture comprising
a) 13 to 20% by weight of polyamide 12 powder;
b) 1 to 5% by weight of stearic acid monoethanolamide;
2 to 6% by weight of glyceryl stearate / or oleate;
c) 3 to 10% by weight of colorant pigment;
20 to 40% by weight of color-neutral or colored pearlescent pigment;
d) 40 to 50% by weight of octamethyl cyclotetrasiloxane;
e) 13 to 20% by weight of cetyl dimethicone copolyol, cetyl dimethicone, polyglyceryl-3-oleate, hexyl laurate.

* * * * *

UNITED STATES PATENT AND TRADEMARK OFFICE
CERTIFICATE OF CORRECTION

PATENT NO. : 5,089,256    Page 1 of 2

DATED : February 18, 1992

INVENTOR(S) : Hans Ulrich SCHELLER et al.

It is certified that error appears in the above-identified patent and that said Letters Patent is hereby corrected as shown below:

Column 1, line 66, after "0 to 20" insert -- % -- .

Column 1, line 67, delete "organ" and insert -- organic -- .

Column 2, line 25, delete "1.00" and insert -- 1.02 -- .

Column 4, line 58, delete "EXAMPLE 1" and insert -- EXAMPLE 1' -- .

Column 5, line 23, after "from" and before "air" insert -- the -- .

Column 5, line 48, delete "custom" and insert -- system -- .

Column 5, line 54, delete "tmeperature" and insert -- temperature -- .

Column 5, line 54, delete "between" and insert -- below -- .

Column 6, line 10, delete "EXAMPLES 2 AND 3" and
          insert -- EXAMPLES 2' AND 3' -- .

Column 6, line 46, delete "0 to °%" and insert -- 0 to 20% -- .

Column 8, line 21, delete "8 to 8%" and insert -- 6 to 8% -- .

UNITED STATES PATENT AND TRADEMARK OFFICE
CERTIFICATE OF CORRECTION

PATENT NO. : 5,089,256

DATED : February 18, 1992

INVENTOR(S) : Hans Ulrich Scheller et al

It is certified that error appears in the above-indentified patent and that said Letters Patent is hereby corrected as shown below:

Column 8, line 67, delete "pasty," and insert -- paste -- .

Column 9, line 11 (Claim 17, line 13), before "13 to 20%" insert -- e) -- .

Signed and Sealed this

Fifth Day of October, 1993

Attest:

BRUCE LEHMAN

*Attesting Officer*  *Commissioner of Patents and Trademarks*